United States Patent
Ansari et al.

[11] 4,011,177
[45] Mar. 8, 1977

[54] CHEMICALS AND THEIR USE IN PERFUMERY

[75] Inventors: Hifzur Rahman Ansari, Rayleigh; Paul Edgar Fido, London; Horst Richard Wagner, Woodford Green, all of England

[73] Assignee: Bush Boake Allen Limited, London, England

[22] Filed: June 5, 1975

[21] Appl. No.: 584,082

[30] Foreign Application Priority Data

June 5, 1974   United Kingdom ............ 24971/74

[52] U.S. Cl. ........................... 252/522; 260/343.6; 260/348 R
[51] Int. Cl.$^2$ ...................................... C07D 307/32
[58] Field of Search ................ 260/343.6; 252/522

[56] References Cited

FOREIGN PATENTS OR APPLICATIONS 2,255,119   5/1973   Germany .......................... 252/522
985,731   3/1965   United Kingdom ............ 260/343.6

OTHER PUBLICATIONS

Rothstein, Bull. Soc. Chim. France [29:3308–3309, 2,80–90 (1935), [cited as C.A. vol. –3309.
Arctander, Perfume & Flavor Chemicals (Montclair, N.J. 1969), Nos. 149, 218, 286, 669, 833, 1105, 1426, 1653, 1728, 1803, 1806, 1870, 2084–2092, 2132, 2279, 2350, 2513, 2877, 3028.
Guenther, Essential Oils (van Nostrand, N.Y., 1952), vol. III, 271–275, 500–504, vol. IV, 701–707, vol. V, 308–315.

*Primary Examiner*—Cecilia Jaisle
*Attorney, Agent, or Firm*—Flynn & Frishauf

[57] ABSTRACT

Compounds having the formula

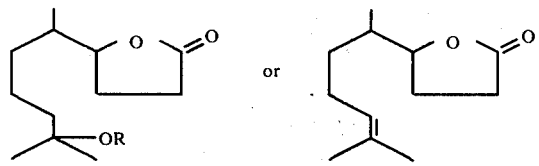

wherein R is an alkyl group having from 1 to 4 carbon atoms are produced by the condensation of the appropriate alkoxylated epoxide with diethyl malonate. The unsaturated compound is formed by the dealkoxylation of an alkoxylated compound. These compounds have attractive fruity-floral type odors and are useful as ingredients of compounded perfumery compositions. The invention also includes perfumery compositions containing at least one of said compounds.

12 Claims, No Drawings

CHEMICALS AND THEIR USE IN PERFUMERY

This invention relates to novel chemicals and their use in compounded perfumery compositions.

From one aspect the invention provides a compound having the formula I

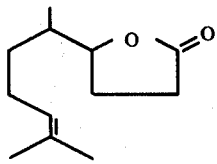

This compound may be an individual diastereoisomer or a mixture of the possible diastereoisomers having the above formula I. (This compound will hereinafter be referred to as citronellene lactone). We have discovered that this compound possesses a powerful fruity-floral peach jasmin type odour of great tenacity. Moreover we have found that it is suitable for blending with a wide range of compounded perfumery compositions.

The compound of formula I may conveniently be prepared by the dealkoxylation of compounds having the formula II

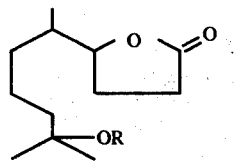

where R is alkyl group having from one to four carbon atoms. Such compounds of formula II will hereinafter be referred to as alkoxycitronellene lactones. The dealkoxylation may be carried out by heating the alkoxycitronellene lactone in the presence of an acid catalyst such as p-toluene sulphonic acid, sulphuric acid, hydrochloric acid, phosphoric acid, etc., at temperatures of from 120° to 130° C in a manner conventional for dealkoxylation reactions.

Such compounds having the formula II are also believed to be novel and constitute a further aspect of the invention. They may be individual diastereoisomers or mixtures of the possible diastereoisomers having the aforesaid formula. Compounds having the formula II have been found to possess a sweet delicate rose-lilly type odour of great tenacity. They are also suitable blending with a wide range of compounded perfumery compositions.

From a further aspect the invention provides a compounded perfumery composition comprising a plurality of odoriferous perfumery ingredients and one or more of the novel compounds having the formula I or II.

The novel perfumery compositions may be compounded according to recognised techniques of perfumery employing known odoriferous perfumery ingredients, e.g., techniques and ingredients mentioned in the standard textbooks "Soap, Perfumery and Cosmetics" by W. A. Poucher, 7th edition, published by Chapman and Hall (London), 1959; "Perfume and Flavour Chemicals" by S. Arctander, published by the author (Montclair) 1959 and "Perfume and Flavour Materials for Natural Origin" also by S. Arctander, self-published, Elizabeth, N.J., 1960. Specific odoriferous ingredients which may be blended with the novel compounds of the invention include 2,6 dimethyl 2 alkoxy octan-7-ol, wherein the alkoxy contains 1 to 6 carbon atoms (as claimed in our copending British Pat. Nos. 52706/71 and 41845/72), and in the corresponding West German Pat. No. 2,225,119, which was published on May 30, 1973 vetivert oil, vetiverol, vetiveryl acetate, guaiac wood oil, guaiac wood acetate, coumarin, musk ketone, lauric aldehyde, benzyl acetate, lemon oil, dimethyl benzyl carbinol, dimethyl benzyl carbinyl acetate, rose absolute, jasmin absolute, ionones, isononyl acetate, methyl phenyl acetate, myrcenyl iso butyrate, β-phenyl ethanol, citronellol, citronellal, hydroxycitronellal, geranium oil, geraniol, linalol, nerol, lavandin oil, linalyl acetate, patchouli oil, petitgrain oil, bergamot oil, heliotropin, ethylene brassylate, undecyl aldehyde, cinnamaldehyde, benzyl salicylate, cinnamyl alcohol, clove bud oil, bay oil, nutmeg oil, pimento berry oil, terpineol, ylang oil, benzyl benzoate, sandalwood oil, clary sage oil, amyl salicylate, labdamun resin, methyl ionones, dihydromyrcenol, orange oil, vanillin, ethylvanillin, olibanum resin, musk ambrette, rhodinol, mandarin oil, methyl nonyl acetaldehyde, neroli oil, cedrol, oakmoss, ω-hydroxy longifolene eugenol, iso-eugenol, cedarwood oil, p-tert-butyl cyclohexyl acetate, styrallyl acetate.

Particularly preferred odoriferous ingredients for blending with the novel compounds having the formula I or II include:

Linalool, linalyl acetate, phenylethyl alcohol, citronellol, geraniol, benzyl acetate, hydroxycitronellal, methoxycitronellall, methyl ionone, amylcinnamic aldehyde, hexylcinnamic aldehyde, amyl salicylate, musk ketone, γnonalactone, αterpineol, aldehydes having 10 to 12 carbon atoms, the essential oils of geranium, lavandin, ylang and bergamot.

It has been found that these compounds blend especially harmoniously with the novel compounds of the invention and compounded perfumery compositions comprising a plurality of odoriferous ingredients including one or more of these preferred materials as aforesaid and one or more of the novel compounds of the invention from a preferred aspect of the invention.

The group R in the novel compounds of formula II may be a methyl, ethyl, n or iso propyl, or n-, sec, or tertiary butyl group. The preferred compound of formula II is that where R is a methyl group.

The novel compounds of the invention may be employed in perfumery compositions in a wide range of proportions say from 0.1 to 95% by weight. A minimum proportion of 0.1 to 5% will be used in most cases.

The compounded perfumery compositions of the invention find use in a wide variety of perfumed materials. For example they may be used in a space spray or can be blended in soap, detergent or deodorant compositions including bath salts, shampoos, toilet waters, or in cosmetic preparations such as cologne waters, toilet waters, face creams, talcum powder, body lotions, sun cream preparations and male toilet products such as fibres, fabrics and paper products.

The novel compounds of the invention having the formula II may conveniently be prepared from the appropriate citronellene epoxide having the formula

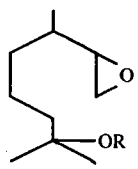

where R is an alkyl group having from 1 to 4 carbon atoms. Such epoxides are obtainable using standard techniques of synthetic organic chemistry as described in West German Pat. No. 2,255,119 which was published on May 30, 1973 and in U.K. Pat. No. 859,568. These epoxides are then condensed with diethyl malonate preferably using the following procedure.

The diethyl malonate is dissolved in a solution of a strong base such as a alkali metal alkoxide or a sodium hydride in an anhydrous solvent. Preferably a solution of sodium methoxide in dry methanol is employed. An equimolar quantity of the appropriate citronellene epoxide is added and the mixture refluxed at a temperature of from 80° to 100° C for a period of from 4 to 12 hours, preferably from 4 to 6 hours. The reaction mixture contains an intermediate ester lactone which is saponified using aqueous alkali and the resulting acid salt acidified and heated to a temperature of from 160° to 180° C whereupon the novel compounds of the invention having the formula II are formed by decarboxylation. These may then be separated from the reaction mixture using conventional techniques such as fractional distillation etc. Yields of up to 80% of the theoretical yield (based upon the weight of the epoxide) are possible.

The invention is illustrated by the following examples:

EXAMPLE 1

Preparation of Methoxycitronellene Lactone.

165 gm of diethyl malonate was added to a solution of 54.5 gm of sodium methoxide in 200 cc of dry methanol at such a rate that steady refluxing was maintained. A solution of 212 gm of methoxycitronellene epoxide in 200 cc of dry methanol was added and the reaction mixture was refluxed for 22 hours. The mixture was then saponified with 30% aqueous sodium hydroxide and subsequently acidified with 10% sulphuric acid. Distillation at 170° to 180° C brought about decarboxylation of the intermediate and 130 gms of methoxycitronellene lactone were obtained.

EXAMPLE 2

Preparation of Citronellene Lactone

The product of Example 1, 130 gms of methoxycitronellene lactone was heated with 4 gms of phosphoric acid at 130° C for 6 hours. The product was then distilled and 90 gms of citronellene lactone were obtained.

EXAMPLE 3

A floral bouquet perfume was made up as follows:

| | |
|---|---|
| Hydroxycitronellal. | 200.0 |
| Phenylethyl Alcohol. | 100.0 |
| g-Methyl Ionone. | 80.0 |
| Hexyl Cinnamic Aldehyde. | 80.0 |
| alpha-Terpineol. | 70.0 |
| Linalool. | 50.0 |
| Citronellol. | 70.0 |
| Methoxycitronellal. | 10.0 |
| Heliotropine. | 30.0 |
| Oil of Ylang. | 30.0 |
| Oil of Geranium. | 20.0 |
| Benzyl Acetate. | 20.0 |
| Benzyl Salicylate. | 100.0 |
| Isoeugenol. | 10.0 |
| Methoxyelgenol. | 40.0 |
| Jasmin Absolute Synthetic. | 20.0 |
| Musk Ketone. | 30.0 |
| Aldehyde C.10 10% in diethylphtalate. | 10.0 |
| Styrallyl Acetate. | 10.0 |
| Citronellene Lactone. | 20.0 |
| | 1000.0 |

EXAMPLE 4

A perfumery concentrate suitable for use as detergent perfume was made up as follows:

| | |
|---|---|
| Phenyl Ethyl Alcohol. | 200.0 |
| Citronellol. | 100.0 |
| Tetrahydro Geraniol. | 30.0 |
| Linalool. | 100.0 |
| Benzyl Acetate. | 50.0 |
| Amyl Salicylate. | 100.0 |
| p-tert-butyl Cyclohexyl Acetate. | 50.0 |
| Terpinyl Acetate. | 50.0 |
| Methoxy elgenol. | 50.0 |
| Valanone. | 30.0 |
| Cinnamic Alcohol. | 20.0 |
| Amyl Cinnamic Aldehyde. | 40.0 |
| Ylang Synthetic. | 40.0 |
| Oil of Lavandin Abrialis. | 20.0 |
| Oil of Patchouli Penang. | 20.0 |
| Dihydromyrcenol. | 10.0 |
| Phenylacetaldehyde dimethylacetal. | 10.0 |
| Aldehyde C.12 MNA 10% in Diethylphtalate. | 10.0 |
| Musk Xylene. | 20.0 |
| Musk Ketone. | 10.0 |
| Coumarin. | 10.0 |
| Methoxycitronellene Lactone. | 30.0 |
| | 1000.0 |

What we claim is:

1. A compound of the formula

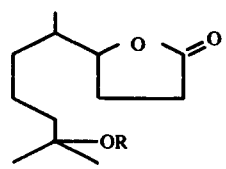

wherein R is an alkyl group having from 1 to 4 carbon atoms.

2. A compound having the formula

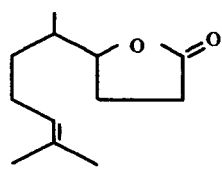

3. A compound according to claim 1 wherein R represents a methyl group.

4. A compound according to claim 1 wherein R represents a group selected from the group consisting of ethyl, n-propyl, iso propyl, n-butyl, sec-butyl and tertiary butyl groups.

5. A compounded perfumery composition comprising ingredient (i) in an amount between 0.1 and 95% by weight of the composition of at least one compound selected from the group consisting of

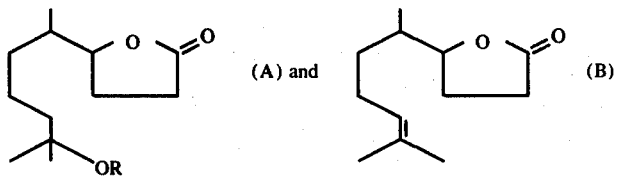

wherein R is an alkyl group having 1 to 4 carbon atoms and ingredient (ii) a plurality of odiferous ingredients in addition to said ingredient (i), said plurality of odiferous ingredients (ii) selected from the group consisting of 2,6-dimethyl-2-alkoxy-octan-7-ol, wherein the alkoxy contains 1 to 6 carbon atoms vetivert oil, vetiverol, vetiveryl acetate, guaiac wood oil, guaiac wood acetate, coumarin, musk ketone, lauric aldehyde, benzyl acetate, lemon oil, dimethyl benzyl carbinol, dimethyl benzyl carbinyl acetate, rose absolute, jasmin absolute, ionones, iso-nonyl acetate, methyl phenyl acetate, myrcenyl iso butyrate, β-phenyl ethanol, citronellol, citronellal, hydroxycitronellal, geranium oil, geraniol, linalool, nerol, lavandin oil, linalyl acetate, patchouli oil, petitgrain oil, bergamot oil, heliotropin, ethylene brassylate, undecyl aldehyde, cinnamaldehyde, benzyl salicylate, cinnamyl alcohol, clove bud oil, bay oil, nutmeg oil, pimento berry oil, terpineol, ylang oil, benzyl benzoate, sandalwood oil, clary sage oil, amyl salicylate, labdamun resin, methyl ionones, dihydromyrcenol, orange oil, vanillin, ethylvanillin, olibanum resin, musk ambrette, rhodinol, mandarin oil, methyl nonyl acetaldehyde, neroli oil, cedrol, oakmoss, ω-hydroxy longifolene eugenol, iso-eugenol, cedarwood oil, p-tert-butyl cyclohexyl acetate, and styrallyl acetate.

6. A composition according to claim 5 wherein said ingredient (i) is at least 0.1% by weight of said perfumery composition.

7. A composition according to claim 5 wherein said ingredient (i) is said compound (A).

8. A composition according to claim 5 wherein said ingredient (i) is said compound (B).

9. A composition according to claim 5 wherein said plurality of odiferous ingredients (ii) contains at least one perfumery ingredient selected from the group consisting of linalool, linalyl acetate, phenyl ethyl alcohol, citronellol, geraniol, benzyl acetate, hydroxycitronellal, methoxycitronellal, methyl ionone, amyl cinnamic aldehyde, hexyl cinnamic aldehyde, amyl salicylate, musk Ketone, γ-nonalactone, α-terpineol, aldehydes having from 10 to 12 carbon atoms, the essential oils of geranium lavandin, ylang and bergamot.

10. A composition according to claim 9 wherein said ingredient (i) is at least 0.1% by weight of said perfumery composition.

11. A composition according to claim 10 wherein said ingredient (i) is said compound (A).

12. A composition according to claim 10 wherein said ingredient (i) is said compound (B).

* * * * *